United States Patent
Harvey et al.

(10) Patent No.: US 8,835,159 B2
(45) Date of Patent: Sep. 16, 2014

(54) STATIC SOLID STATE BIOREACTOR AND METHOD FOR USING SAME

(75) Inventors: Jeffrey T. Harvey, Lakewood, CO (US); Murray D. Bath, Centennial, CO (US); Glenn R. Sprenger, Golden, CO (US); Edward Ogrodny, Paonia, CO (US)

(73) Assignee: Geosynfuels, LLC, Golden, CO (US)

( * ) Notice: Subject to any disclaimer, the term of this patent is extended or adjusted under 35 U.S.C. 154(b) by 0 days.

(21) Appl. No.: 13/474,574

(22) Filed: May 17, 2012

(65) Prior Publication Data

US 2012/0258512 A1 Oct. 11, 2012

Related U.S. Application Data

(63) Continuation of application No. 12/423,803, filed on Apr. 14, 2009, now abandoned.

(51) Int. Cl.
| | | |
|---|---|---|
| C12M 1/00 | (2006.01) |
| C12M 1/02 | (2006.01) |
| C12M 1/10 | (2006.01) |
| C12P 5/02 | (2006.01) |
| B09B 3/00 | (2006.01) |
| C05F 17/02 | (2006.01) |
| C12M 1/107 | (2006.01) |
| C12M 1/16 | (2006.01) |
| C12M 1/26 | (2006.01) |
| C12P 7/06 | (2006.01) |

(52) U.S. Cl.
CPC . *C12P 5/023* (2013.01); *B09B 3/00* (2013.01); *C05F 17/0247* (2013.01); *C05F 17/0276* (2013.01); *C05F 17/027* (2013.01); *C12M 21/04* (2013.01); *C12M 21/16* (2013.01); *C12M 23/02* (2013.01); *C12M 23/36* (2013.01); *C12M 29/02* (2013.01); *C12M 33/14* (2013.01); *C12M 33/16* (2013.01); *C12P 7/06* (2013.01); *Y02E 50/17* (2013.01); *Y02E 50/343* (2013.01); *Y02E 50/16* (2013.01)
USPC .................. 435/290.4; 435/290.2; 435/162; 435/167; 210/626

(58) Field of Classification Search
CPC .... C05F 17/02; C05F 17/027; C05F 17/0229; C05F 17/0247; B09B 3/00; C12P 5/023; C12M 21/04; C12M 21/16; C12M 23/02; C12M 23/36; C12M 33/14; C12M 33/16; Y02E 50/17; Y02E 50/16; Y02E 50/343
USPC ........ 435/157, 161, 170, 289.1, 290.1–290.4; 210/626
See application file for complete search history.

(56) References Cited

U.S. PATENT DOCUMENTS 4,758,344 A * 7/1988 Wildenauer .................. 210/603
5,258,306 A * 11/1993 Goldfarb .................. 435/290.2

(Continued)

OTHER PUBLICATIONS

International Searcch Repoprt and the Written Opinion of the International Searching Authority, dated Aug. 23, 2010, for corresponding PCT Application PCT/US2010/31128, Filed Apr. 14, 2010.*

*Primary Examiner* — Michael Hobbs
(74) *Attorney, Agent, or Firm* — Sheppard Mullin Richter & Hampton LLP

(57) ABSTRACT

A static solid state bioreactor and method of using same. The bioreactor comprises a vessel having an upper end and a lower end, the upper end having a sealable opening. A gas distribution system in communication with the upper end and the lower end of the vessel. A liquid distribution system in communication with the upper end of the vessel. A liquid recovery system in communication with the lower end of the vessel. A material removal system disposed at the lower end of the vessel for removing biomass from the vessel.

24 Claims, 14 Drawing Sheets

(56) References Cited

U.S. PATENT DOCUMENTS

| | | |
|---|---|---|
| 5,645,726 A | 7/1997 | Pollock |
| 6,733,663 B1 * | 5/2004 | Simon et al. ............ 210/104 |
| 2004/0058435 A1 * | 3/2004 | Ueda et al. ............ 435/290.1 |
| 2009/0020475 A1 | 1/2009 | Jordan |

* cited by examiner

STATIC SOLID STATE BIOREACTOR AND METHOD FOR USING SAME

CROSS REFERENCE TO RELATED APPLICATIONS

This is a continuation application of U.S. patent application Ser. No. 12/423,803, filed Apr. 14, 2009 now abandoned, which is incorporated herein by reference.

FIELD

The present patent document relates to static solid state bioreactors and methods for using the same.

BACKGROUND

Fermentation may be broadly defined as the controlled cultivation of microorganisms for the transformation of an organic compound into a new product. Therefore, the term "fermentation" includes conventional alcohol fermentation, which is typically performed using some type of living ferment, such as yeast, and involves the enzymatically controlled anaerobic conversion of simple sugars, including those produced through saccharification, into carbon dioxide and alcohol. Depending on the organic compounds employed and fermentative microorganism(s) employed, however, a host of other fermentation products may be generated in addition to, or in the alternative to, alcohol.

Recently, conversion of biomass through fermentation into ethanol or other useful products as a replacement for fossil fuels has garnered considerable attention. Biomass for such conversion processes can be potentially obtained from numerous different sources, including, for example, wood, paper, agricultural residues, food waste, herbaceous crops, and municipal and industrial solid wastes to name a few.

For a number of reasons, biomass is an attractive feedstock for producing fossil fuel substitutes. Biomass has a smaller carbon footprint than conventional fossil fuels because it typically comes from plants that have an annual growth cycle; therefore, the carbon dioxide liberated by the combustion of the derived fuel is subsequently reused through photosynthesis by the plant's regrowth and results in no net carbon dioxide in the earth's atmosphere. Further, biomass is readily available and the conversion of biomass provides an attractive way to dispose of many industrial and agricultural waste products. Finally, biomass is a renewable resource because crops may be grown on a continuous basis, utilizing the liberated carbon dioxide each cycle.

While biomass has the potential to provide an attractive fossil fuel alternative, substantial difficulties still remain. Because the main product of the fermentation is a commodity, namely fuel, production costs must be extremely low to be competitive with other fuels. In addition, a main goal of using biomass as a fossil fuel replacement is to reduce carbon pollution. Therefore, any conversion process used should require low energy input. Because the United States alone consumes approximately nine (9) million barrels of gasoline each day, the process of creating a usable fossil fuel replacement from biomass must be scalable to be a meaningful alternative.

Fermentation processes can be divided into two main categories, solid state fermentation (SSF) processes and submerged liquid fermentation (SLF) processes. Solid state fermentation processes involve growth of microorganisms on moist, solid biomass particles. The spaces between the particles contain a continuous gas phase and a non-saturated water phase. Thus, although droplets of water may be present between the particles in a solid state process, and there may be thin films of water at the particle surface, the inter-particle water phase is discontinuous and most of the inter-particle space is filled by the gas phase. The majority of water in the system, therefore, is absorbed within the moist solid particles. In submerged liquid processes by contrast, particles are disposed in a continuous liquid phase.

Although SSF has been practiced for hundreds of years in the preparation of traditional fermented foods, its application to the production of fermentation products within the context of modern biotechnology has been fairly limited. This is because historically it has been notoriously difficult to control the fermentation conditions within SSF. In practice, for example, temperature control, fluid channeling, excessive pressure drop, and evaporation have posed major problems to the development of a commercially viable SSF reactor and process that is suitable for large scale, industrial applications. Thus, while the process of SSF has been practiced at small, batch, scale in the Asian food and beverage industry for hundreds of years to make soy sauce and sake and research has been conducted more recently to produce other products such as enzymes, most fermentation processes used today are still carried out in SLF processes. Indeed, all commercial fermentation processes used for producing alternative fuels that exist today employ a SLF process.

Numerous drawbacks exist with using the SLF process, however. Two principal drawbacks of SLF processes is that they tend to be capital intensive and have high operating costs, making them less than optimum for producing many fermentation products, including alternative fuels, such as ethanol, on an industrial scale and at a competitive price.

If the foregoing problems associated with SSF could be resolved, or at least sufficiently ameliorated, a commercially viable SSF bioreactor and process that is suitable for large scale, industrial applications could be achieved. Such a SSF bioreactor and process could provide several advantages over existing SLF technologies, including high product yield, low cost, ease of use, and scalability.

A wide variety of apparatus have been tried as SSF bioreactors. These apparatus fall into two main categories: static systems and stirred systems. Stirred systems have a means for mixing the biomass during the fermentation process. Stirring adds complexity and significant cost to the bioreactor. This becomes especially true for a bioreactor device that is required to be scaled up to an industrial scale to support, for example, the fossil fuel alternative market.

Static systems are sometimes used because the microorganism used in the fermentation process can not withstand the disruption caused during stirring. Various static bioreactors for SSF have been designed and used including, flasks, petri dishes, columns and trays. These designs have been mostly for laboratory use and are not effective or efficiently designed to be scaled for use at an industrial level.

One of the major problems in utilizing a static SSF bioreactor on a large scale is temperature control. The fermentation of organic compounds in general, and sugars contained or released from biomass in particular, is an exothermic reaction, generating heat in the local area of the microorganism performing the conversion. This leads to localized elevated temperatures within the biomass in the reactor. The elevated temperatures within the SSF bioreactor can result in temperatures well above the optimum for microbial growth, which in turn can inhibit the fermentation process from occurring efficiently. Accordingly, a need exists for a SSF bioreactor design and method of using the same that permits temperature within the bioreactor to be maintained within acceptable process limits during the conversion process.

When a large volume of reacting biomass is confined to a conventional solid state reactor, large temperature gradients are established within the biomass volume. This is primarily due to the fact that it is difficult to remove the localized heat uniformly from the biomass using a remote heat sink. For example, if the walls of the bioreactor are a heat sink, a temperature differential will form radially from the center outward towards the walls. With scale-up, the conduction effect of the walls of the bioreactor will have little effect on the biomass in the center of the reactor and the radial temperature gradient will increase.

Temperature gradients also form in the axial direction. As the fermentation begins, heat from the exothermic reaction tends to rise. This creates a temperature gradient in the axial direction with the top of the biomass being hotter than the bottom.

In an attempt to control the temperature of the biomass, SSF bioreactors have been designed with forced aeration. The convection and evaporation effects of the gas as it passes through the biomass have been used to reduce the temperature. Air or gas is introduced at the bottom of the biomass in the SSF and flowed to the top. By controlling the temperature and humidity of the inlet gas, the biomass in the SSF can be cooled or heated respectively.

Numerous problems exist with present forced aeration bioreactor designs. First, the gas introduced at the bottom of the reactor tends to reduce the temperature of the biomass near the bottom of the reactor, but has a lesser effect on the biomass as it passes up through the reactor. As gas is introduced, it absorbs heat from the biomass at the bottom of the reactor, which in turn raises the temperature and humidity of the gas, and makes it less effective at cooling as it passes up through the reactor. This tends to bring the temperature of the biomass at the bottom of the reactor into equilibrium with the temperature of the input gas and creates an increasing temperature gradient as the height of the biomass increases. These effects are exacerbated as the height of the SSF increases. Furthermore, the pressure drop typically increases as the height increases making forced aeration more difficult.

Because of the problems with heat removal in forced aeration SSF bioreactors, the height of the bioreactor and therefore the height of the biomass has been kept low. It has been suggested that the height of the biomass in a forced aeration SSF bioreactor should not exceed one (1) meter. See D. A. Mitchell, et al., *Solid State Fermentation Bioreactors, Fundamentals of Design and Operation*, Chpt. 7, 93 (2006). This creates a problem, however, because by keeping the height small, large areas are required in order to scale up existing bioreactor designs, which in many cases will be impracticable due to the availability and/or cost of the required land.

One proposed solution to the height problem is suggested by Suryanarayan et. al. in U.S. Pat. No. 6,664,095 B1. The Suryanarayan patent suggest a tray stacking solution whereby the height of the biomass in each individual tray is kept small and a plurality of trays are stacked on top of each other. While this solution effectively keeps the height of the biomass small while allowing the bioreactor to increase in height, the tray stacking design and implementation is too expensive and impractical to scale to the industrial levels necessary for many potential applications, including for cost effective alternative fuel production.

A further problem with forced aeration SSF reactors is the drying effect of the aeration process. The water content of the biomass must be maintained. If the biomass becomes too dry, the efficiencies of the fermentation processes are reduced. Even if the gas entering the bioreactor is completely saturated, the biomass absorbs the moisture from the gas as it passes from the bottom of the bioreactor to the top and the resultant gas has a drying effect on the biomass. Further, the increase in temperature towards the top of the bioreactor can cause further evaporation, drying the biomass more.

In addition to the reduced efficiency of the fermentation processes, the drying of the biomass has a secondary effect. As the bed dries it will contract and reduce in volume. This reduction in volume will cause channeling and cause the biomass to pull away from the sides of the reactor. Channeling occurs when paths of lower resistance develop through the bed and the forced aeration flows through the bed along the channels only, rather than being evenly dispersed through the bed. Channeling can occur along the boundary between the reactor and the biomass or through the biomass itself. Channeling reduces the flow of gas to large parts of the volume of biomass causing localized temperature increases and an overall increase in the temperature gradients and thus, a reduction in process efficiency. As the bioreactor is scaled up, the bioreactor walls, which can be used as heat sinks, have less intimate contact with the biomass, increasing the temperature gradients in the radial direction.

Further, contemporary thinking is that liquid can not be effectively used in a static SSF bioreactor because the liquid can not be evenly dispersed throughout the biomass. The addition of liquid to static SSF reactors can result in flooding and inhibit the fermentation process. The permeability of biomass, depending on the source, is usually very limited and tends to decrease as the biomass depth is increased. Further, as the biomass is fermented, the biomass degrades, its volume decreases, and its density increases, further reducing permeability and inhibiting fluid flow.

Stirring or otherwise mixing the biomass in the bioreactor can reduce channeling, help eliminate temperature gradients, allow liquid to be added to the biomass, and more evenly distribute the moisture in the reactor. While stirring can have positive effects, stirring mechanisms are complicated to build and become extremely expensive to construct and operate when scaled. Even if stirring equipment on a large scale is effectively designed, the process of stirring will be extremely expensive for a large scale SSF reactor. Wet biomass requires large amounts of energy to mix or stir because of its weight. In addition, as mentioned above, stirring can have a deleterious effect on the microorganisms used in the fermentation process.

In view of the foregoing, a need exists for an improved static solid state bioreactor that addresses or at least ameliorates one or more of the problems associated with existing SSF bioreactor designs.

Saccharification is the process of breaking down a complex carbohydrate (such as starch, cellulose or hemicellulose) into its monosaccharide components or sugars. Saccharification can be facilitated via the use of chemical reagents, biological agents, or combinations of these two. During alternative fuel production processes, the converted biomass is typically subjected to a saccharification process prior to or simultaneous with the fermentation process used to convert the simple sugars in the biomass, including those released through saccharification, into carbon dioxide and alcohol and/or methane. Accordingly, because one of the major potential applications of an industrial scale static SSF bioreactor is the production of alternative fuels, such as ethanol and/or methane, it would be beneficial if such a bioreactor could also be used for saccharification of biomass, either separate from the fermentation process or simultaneous with the fermentation process.

SUMMARY OF THE INVENTION

In view of the foregoing, an object according to one aspect of the present patent document is to provide an improved static solid state bioreactor that may be used for solid state fermentation of biomass. Preferably the bioreactor is also suitable for saccharification of complex carbohydrates in biomass. To this end, a static solid state bioreactor is provided that comprises: a vessel having an upper end and a lower end, the upper end having a sealable opening; a gas distribution system in communication with the upper end of the vessel and the lower end of the vessel; a liquid distribution system in communication with the upper end of the vessel; a liquid recovery system in communication with the lower end of the vessel; and a material removal system disposed at the lower end of the vessel for removing biomass residue from the vessel.

The bioreactor may further comprise a plurality of openings located on the lower end of the vessel that allow the gas distribution system to communicate with the vessel. The liquid recovery system may also communicate with the vessel through a plurality of openings on the lower end of the vessel.

According to a further embodiment, the lower end of the vessel may be conically shaped. In one implementation, the lateral wall of the conically shaped lower end includes a plurality of openings to allow communication with the gas distribution system and/or the liquid recovery system at the lower end. In such an embodiment, the communication with the gas distribution system and liquid recovery system can be spread out over a large area, namely the surface of the conically shaped lower end, while at the same time the biomass may be directed towards a material removal system disposed at the apex of the conically shaped lower end. The conically shaped lower end, therefore, allows for even distribution of gas and liquid while facilitating easy and efficient material removal from the bioreactor.

According to a further embodiment, the material reclaim system of the bioreactor may comprise an auger driven by a motor. If for example the vessel is cylindrical, the auger may extend radially from the center of the vessel towards and outer wall and be rotateable around the vessel. In a second example, where the vessel has a conically shaped lower end, the auger may protrude into the vessel through a biomass opening at the apex of the conically shaped lower end and extend up towards a perimeter of the base of the conically shaped lower end. The auger would likewise rotate about the axis of the vessel drawing material down and towards the biomass opening at the apex.

According to yet another embodiment, the bioreactor comprises a plurality of screens, each screen being configured to fit within and cover one of the plurality of openings in the lower end. The screens are used to cover the openings and prevent biomass from escaping the vessel and entering the liquid recovery system or the gas distribution system. The screen spacing is preferably sufficiently small to substantially inhibit solids within the bioreactor from escaping through the screen, while at the same time allowing the free flow of liquid and gas through the screens. This prevents any biomass that might penetrate through the screen from clogging the duct or tube used in the liquid recovery system or gas distribution system.

According to a further embodiment, the screen used to cover the openings in the lower end of the vessel comprises a wedge wire screen. The design of the wedge wire screen ensures that biomass does not get stuck in the spaces or holes between the wires of the screen but passes through. This prevents biomass from clogging the screen and preventing the passage of gas or liquid through the screen.

According to a further embodiment, the screens used to cover the openings in the lower end of the vessel can have wires running in a direction towards the biomass opening and material recovery system. Thus, in a conically shaped lower end, the screen wires would run from the apex to the perimeter of the base. Aligning the wires of the screens in the direction of material removal aids the material recovery system and minimizes the likelihood of forming blockages in the screen as the solids in the bioreactor move across the screen. If the wires run in a perpendicular direction, they can act like a grate, hampering material removal and increasing the likelihood that the screens will become damaged during operation of the bioreactor.

According to a further embodiment, the bioreactor's gas distribution system further comprises a first duct, a second duct, and at least one fan. The first duct is in communication with the upper end of the vessel and the fan and the second duct is in communication with the lower end of the vessel and the fan. The ducts can be made from a single piece or a plurality of pieces. The ducts allow the fan to communicate with the upper and lower ends of the vessel. Preferably the gas distribution system comprises one or more valves for selectively connecting the intake and output of the fan to the first and second ducts, respectively, thereby allowing the gas distribution system to change the direction of gas flow through the vessel.

According to a further embodiment, the liquid distribution system of the bioreactor may be in communication with the liquid recovery system. By connecting the liquid distribution system with the liquid recovery system, liquid effluent from the biomass can be recycled. Because the effluent from the biomass may contain sugars or other organic compounds that have not been fermented yet, recycling the liquid effluent allows for a more complete and efficient fermentation process.

According to another aspect of the present patent document, a method of performing static solid state fermentation is provided. The method comprises: mixing a bulking agent with biomass; adding the mixture to a static solid state bioreactor; irrigating the mixture with an aqueous solution; flowing gas through the mixture; and maintaining a microorganism supporting environment within the bioreactor by managing the flow of the aqueous solution and the gas through the mixture and periodically switching the direction of gas flow through the bioreactor.

Prior to adding the mixture to a static solid state bioreactor a number of additives and reagents may be added to the biomass to improve or supplement fermentation of the biomass including: 1) adding an inoculum comprising one or more microorganism to the biomass; 2) adding one or more enzymes to the biomass; and 3) adding an antibiotic to the biomass.

Once the biomass is prepared for fermentation and the mixture is added to the bioreactor, the mixture may be irrigated with water to maintain a desired moisture content within the biomass or to heat or cool the mixture. Aqueous solution that flows through the biomass is discharged into the fluid recovery system, which collects the effluent discharge and may recycle it back onto the biomass within the bioreactor.

In order to allow fluid flow through the biomass (both gas and liquid) it is desirable that a certain hydraulic conductivity be maintained within the reactor throughout the fermentation process. This is accomplished through the use of the bulking agent. Preferably, the composition, size, and amount of bulking agent mixed with the biomass is selected to maintain a hydraulic conductivity of the biomass greater than $10^{-4}$ cm/sec throughout the fermentation process.

According to yet another aspect, a non-stirred solid state bioreactor is provided that comprises, a hollow body in which a mixture of biomass and a bulking agent is stacked. The stacked biomass is stored within the hollow body under conditions suitable for fermentation. The hollow body has a lower end and an upper end. The lower end is perforated to allow the flow of gas and liquid through the stacked biomass. The upper end has at least one sealable opening for stacking the biomass within the hollow body. A passageway for removal of the decomposed biomass material is provided at the lower end of the hollow body. A material removal system is operatively provided within the hollow body at the lower end. The material removal system is configured to direct the flow of decomposed biomass material toward the passageway during unloading of the hollow body. A gas delivery system is coupled to the upper and lower ends of the hollow body and is configured to flow gas through the stacked biomass in both directions, from the lower end to the upper end and from the upper end to the lower end. An irrigation system is disposed within the hollow body proximate to the upper end of the hollow body and is configured to irrigate the stacked biomass from above. A system for collecting liquid effluent that drains from the stacked biomass is operatively provided proximate to the perforated lower end.

According to one embodiment, the material removal system comprises at least one auger to remove the material from the hollow body.

In yet another embodiment, the vessel may be sealed for anaerobic bioreactor operation.

According to yet another aspect of the present patent document, a bioreactor for performing static solid state fermentation of biomass is provided. The bioreactor according to this aspect comprises, a vessel having an upper end and a lower end, the lower end having a plurality of openings and a material removal port. A plurality of gas ports are in communication with a gas distribution system and in communication with the plurality of openings in the lower end of the vessel. A plurality of liquid ports are in communication with a liquid collection system and in communication with the plurality of openings in the lower end of the vessel. At least one screen is disposed in the lower end of the vessel covering the plurality of openings.

In one embodiment, the bioreactor may further comprise a plurality of manifolds, the plurality of manifolds being disposed to connect the plurality of openings with the plurality of gas ports and the plurality of liquid ports. Preferably at least one gas port is located above at least one liquid port on at least one manifold. This allows the liquid to naturally separate from the gas and enter the liquid recovery system while minimizing the amount of liquid that enters the gas distribution system.

As described more fully below, the static solid state bioreactor designs and methods for using same may readily and cost effectively be scaled for large industrial applications such as biofuels production. Further aspects, objects, desirable features, and advantages of the bioreactors and methods disclosed herein will be better understood from the detailed description and drawings that follow in which various embodiments are illustrated by way of example. It is to be expressly understood, however, that the drawings are for the purpose of illustration only and are not intended as a definition of the limits of the claimed invention.

DETAILED DESCRIPTION OF THE PREFERRED EMBODIMENTS

In the following description of the preferred embodiment, reference is made to the accompanying drawings that form a part hereof, and in which is shown by way of illustration a specific embodiment in which the invention may be practiced. It is to be understood that other embodiments may be utilized and structural changes may be made without departing from the scope of the present invention.

Consistent with its ordinary meaning as a renewable energy source, the term "biomass" is used herein to refer to living and recently dead biological material including carbohydrates, proteins and/or lipids that can be converted to fuel for industrial production. By way of non-limiting example, "biomass" can refer to plant matter, biodegradable solid waste such as dead trees and branches, yard clippings, recycled paper, recycled cardboard, and wood chips, plant or animal matter, and other biodegradable wastes.

Figure 1:
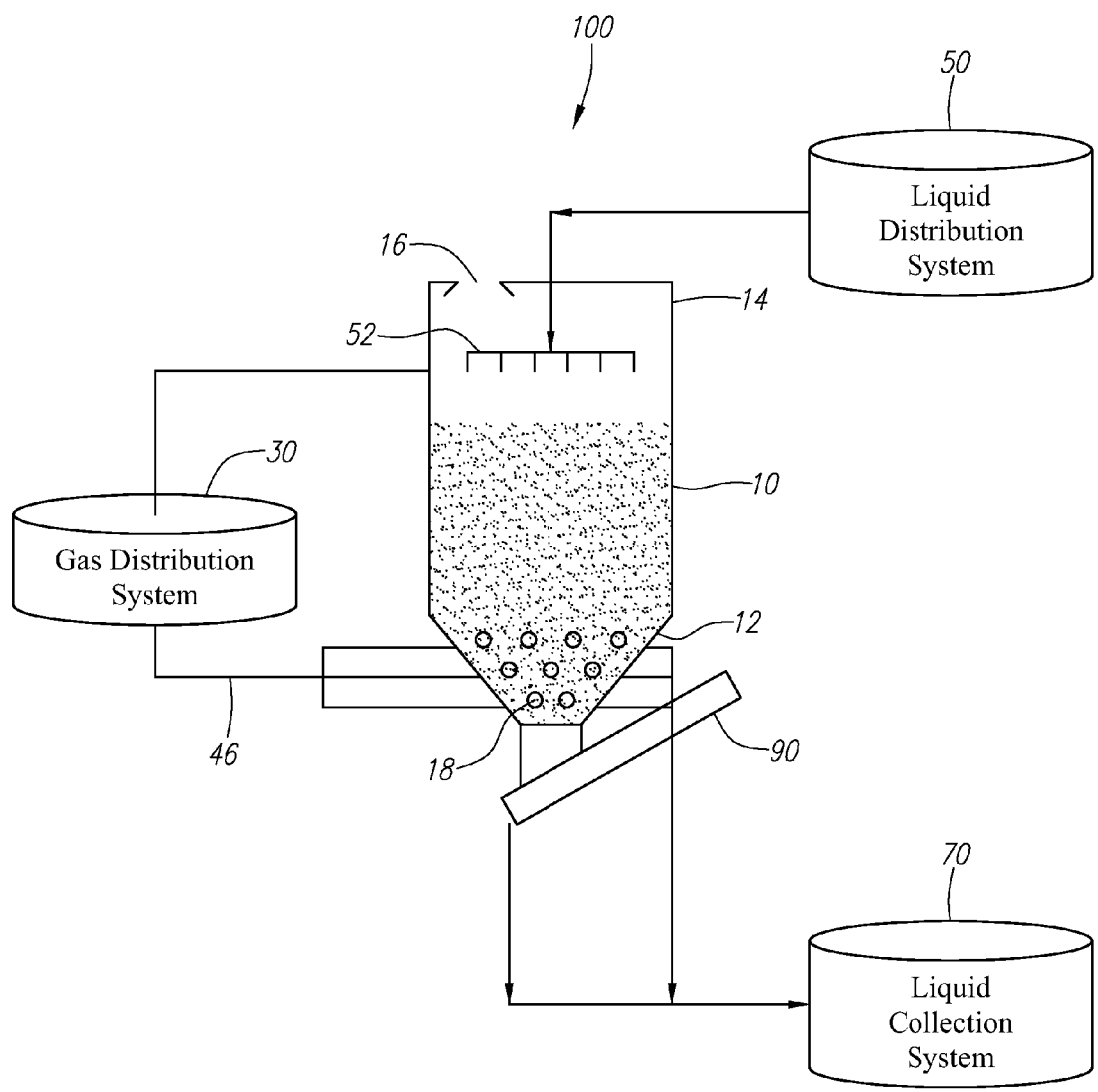
FIG. 1 schematically illustrates a bioreactor for performing static solid state saccharification and/or fermentation of biomass.

FIG. 1 illustrates a schematic view of a bioreactor for performing static solid state saccharification and/or fermentation of biomass. Bioreactor 100 comprises vessel 10, gas distribution system 30, liquid distribution system 50, liquid recovery system 70, and material removal system 90.

As shown, vessel 10 has a cylindrical shape. Cylindrical is a preferred shape as it facilitates the design of a suitable material removal system 90. The vessel 10, however, is not limited to any particular shape and may be, for example, square, triangular, rectangular, octagonal, or any other suitable multi-sided shape or hollow body without departing from the scope of the present invention. Vessel 10 can be made from various materials, or material combinations, including, stainless steel, steel, aluminum, other metals, concrete, wood, plastic or plastic derivatives, or other basic building material.

Vessel 10 may be constructed using any construction techniques suitable for large vessels. Depending on its size, for example, vessel 10 may be constructed from a single piece or from a frame and liner type construction. If the vessel 10 is to be used for an anaerobic fermentation process, such as the production of alcohol or methane, then the vessel 10 is preferably sealable to provide a gas-tight environment, as maintaining an anaerobic environment in such processes is critical to achieving an efficient bioreactor 100.

While vessel 10 can be any size, the vessel 10 is preferably of a size suitable for industrial scale. Accordingly, the vessel 10 preferably is preferably greater than 1 meter high and greater than 1 meter in diameter. More preferably, the height of vessel 10 is 3 meters or higher, and even more preferably 6 meters or higher. The diameter of a 6 meter vessel 10 may be, for example, greater than 9 meters or greater in diameter and even more preferably 15 meters or greater in diameter. Common existing structures may be retrofitted to make them gas tight for use as vessel 10, including large tanks, covered lagoons, grain silos, or other large enclosures.

Vessel 10 comprises a lower end 12 and an upper end 14. Vessel 10 further comprises a sealable opening 16 in the upper end 14. The sealable opening is used for loading the biomass into the vessel 10. The biomass can be loaded via a tripper conveyor or screw feeder discharging through the sealable opening 16 in the upper end of the vessel 10. The opening 16 may be sealed using automatic doors to create an anaerobic environment.

Before the biomass is loaded into the vessel 10 for fermentation, a number of reagents and additives may be added. For example, the production of alternative fuels from biomass may require additional processes, other than fermentation, such as saccharification. Saccharification may be required if the biomass does not already contain sufficient free fermentable sugars. Saccharification can be induced by adding enzymes to release the sugars for further fermentation. The enzymes hydrolyze the complex sugars present in the biomass, converting them to simple fermentable sugars. Depending on the biomass to be converted, different amounts or combinations of enzymes may be needed. Saccharification and fermentation can occur simultaneously in the bioreactor or in series. Different types of biomass may require the addition of different additives before entering the bioreactor.

Once the biomass contains free fermentable sugars, the actual microorganism, ferment or fermentation agent, can begin to convert the free fermentable sugars to alcohol, such as ethanol, or methane. The fermentation agent in the context of alcohol fermentation is typically a yeast that converts the simple sugars into ethanol.

The fermentation agent may require the addition of nutrients for more efficient propagation. Blended complex yeast nutrients that supply ammonia salts, alpha amino nitrogen, sterols, unsaturated fatty acids, other key nutrients, and inactive yeast are commercially available.

In order to suppress the proliferation of undesirable microorganisms, that produce unwanted products and reduce ethanol yield, one or more antibiotic substances can be added. Once the biomass is prepared with the additives and reagents a bulking agent can be added to increase and maintain the hydraulic conductivity of the biomass.

As shown in FIG. 1, bioreactor 100 further comprises a material removal system 90 disposed at the lower end 12 of the vessel 10. The material removal system is used to remove the biomass residue from the vessel 10 when saccharification and fermentation has finished. The material removal system can be designed in a number of ways. If the vessel is suspended above the ground, a hinged base plate(s) could be used to dump the material out of the vessel 10. A portion of the side of the vessel 10 along the lower end 12 could be opened and a mechanical device, such as a backhoe, could be used to remove the biomass residue. A tube could be inserted through a hole in the lower end 12 and the biomass could be vacuumed out.

Although FIG. 1 shows but a single instance of a bioreactor 100, numerous instances can be used in combination. In particular, a plurality of vessels 10, gas distribution systems 30, liquid distribution systems 50, liquid recovery systems 70, and material removal systems 90 can be used and interconnected. Not only can the overall design be duplicated, but individual components can likewise be duplicated. For example, a plurality of vessels 10 could be used in communication with a single gas distribution system 30, and liquid distribution system 50.

Figure 2:
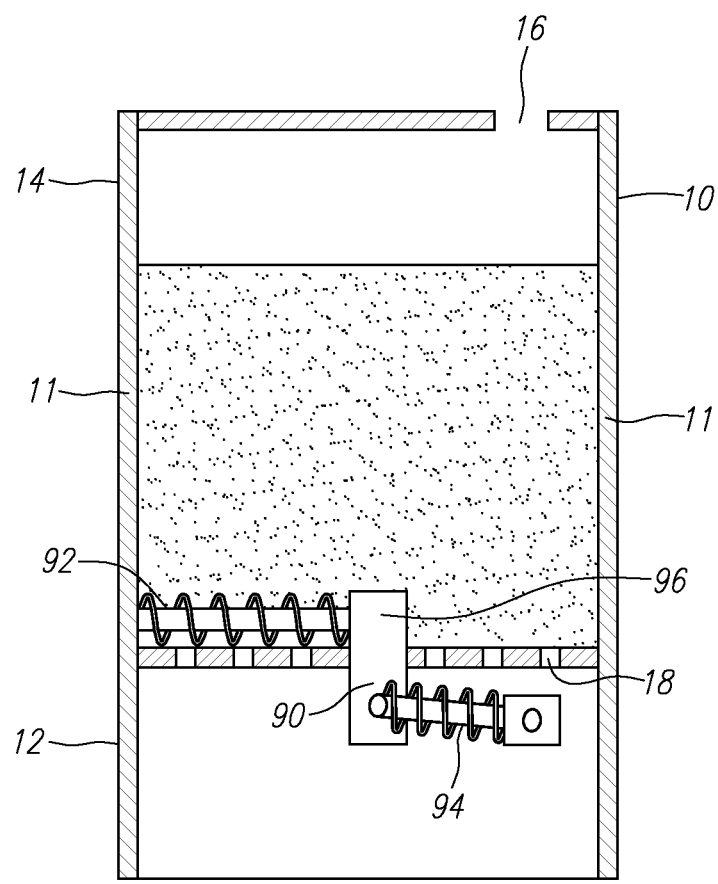
FIG. 2 illustrates a cross sectional view of a vessel for use in a bioreactor for performing static solid state saccharification/fermentation of biomass with a material removal system further comprising at least one auger.

FIG. 2 illustrates a cross sectional view of a vessel 10 for use in a bioreactor for performing static solid state saccharification and/or fermentation with a material removal system further comprising at least one auger. As shown in FIG. 2 a vessel 10 has a material removal system 90 further comprising an auger 92. The auger is located at the lower end 12 of the vessel 10 and can rotate around the vessel 10 drawing biomass towards the center and out through an opening into a hopper 96. The hopper 96 is not required and the material could be removed directly into a truck or onto a conveyer for transport. If a hopper 96 is used a second auger (discharge auger) 94 may be employed to remove the material from the hopper 96. Material removal systems similar to the ones described can be obtained from Laidig Systems, Inc. 14535 Dragoon Trail, Mishawaka Ind. 46544.

The biomass conversion reactions generate heat but they may also require a specific temperature to initiate. This presents a new problem because the SSF reactor has to be heated to its ideal starting temperature before significant conversion reactions will take place. Therefore, sometimes it may be advantageous to be able to restrict heat loss from the bioreactor.

As shown in FIG. 2, in order to help prevent heat loss, the walls 11 of the vessel 10 may be insulated to better control the temperature in the bioreactor 10. The outside of the vessel 10 will be a heat sink if the walls 11 are not insulated and radial temperature gradients may form. The walls can be insulated on the inside as shown in FIG. 2, or on the outside. Insulation can be made from common insulation materials such as blankets, spray foams, fiberglass, or other materials that can be used to cover, line, or separate the walls of the reactor from the biomass and prevent or reduces the passage, transfer, or leakage of heat.

As well as passive heat protection such as insulating the walls, the bioreactor may employ active heating like an electric heater.

Returning to FIG. 1, the bioreactor 100 further comprises a gas distribution system 30 for flowing a gas through the vessel 10. The fermentation of sugars produces ethanol and carbon dioxide. The atmosphere in the newly-loaded bioreactor 100 starts off as air but as fermentation proceeds, the carbon dioxide generated rapidly displaces the air, resulting in an essentially complete carbon dioxide environment. Alternatively, the initial air atmosphere in the bioreactor 100 may be displaced by introducing carbon dioxide from an outside source. One example would be from an adjacent bioreactor.

A gas distribution system 30 helps manage the heat and control temperatures in the bioreactor 100 and maintains the desired gaseous environment for saccharification and fermentation. In addition, the gas distribution 30 system is an integral part of collecting the product of the biomass conversion.

The gas leaving the solid state bioreactor will contain much of the desired product of the biomass conversion. The low vapor pressure of the alternative fuels produced in the bioreactor tend to cause them to evaporate into the gas stream at levels proportionate to their concentration in the bioreactor liquid phase. The higher the temperature and the higher the liquid fuel concentration, the greater the effect.

The gas distribution system 30 is in communication with the upper end 14 and the lower end 12 of the vessel 10, via duct 46 and can force a flow of gas from the lower end 12, through the vessel 10, and out the upper end 14. As shown in FIG. 1, the gas distribution system 30 is in communication with the lower end 12 of the vessel 10 through a plurality of openings 18.

Combined with the gas distribution system 30, the natural evolution of warm carbon dioxide during fermentation results in an upward gas flow of gas in the vessel 10. This gas flow carries with it heat and moisture and causes a axial temperature gradient to form in the vessel 10 such that the biomass in the upper end 14 is hotter than the biomass in the lower end 12. Utilizing a downward forced gas flow allows the gas to be removed from the lower end 12 of the vessel 10 and mitigates the temperature gradient. Therefore, in the preferred embodiment, the gas distribution system 30 can also reverse the direction of the flow of gas through the vessel 10 to enter at the upper end 14 and exit from the lower end 12 of the vessel 10.

Figure 3:
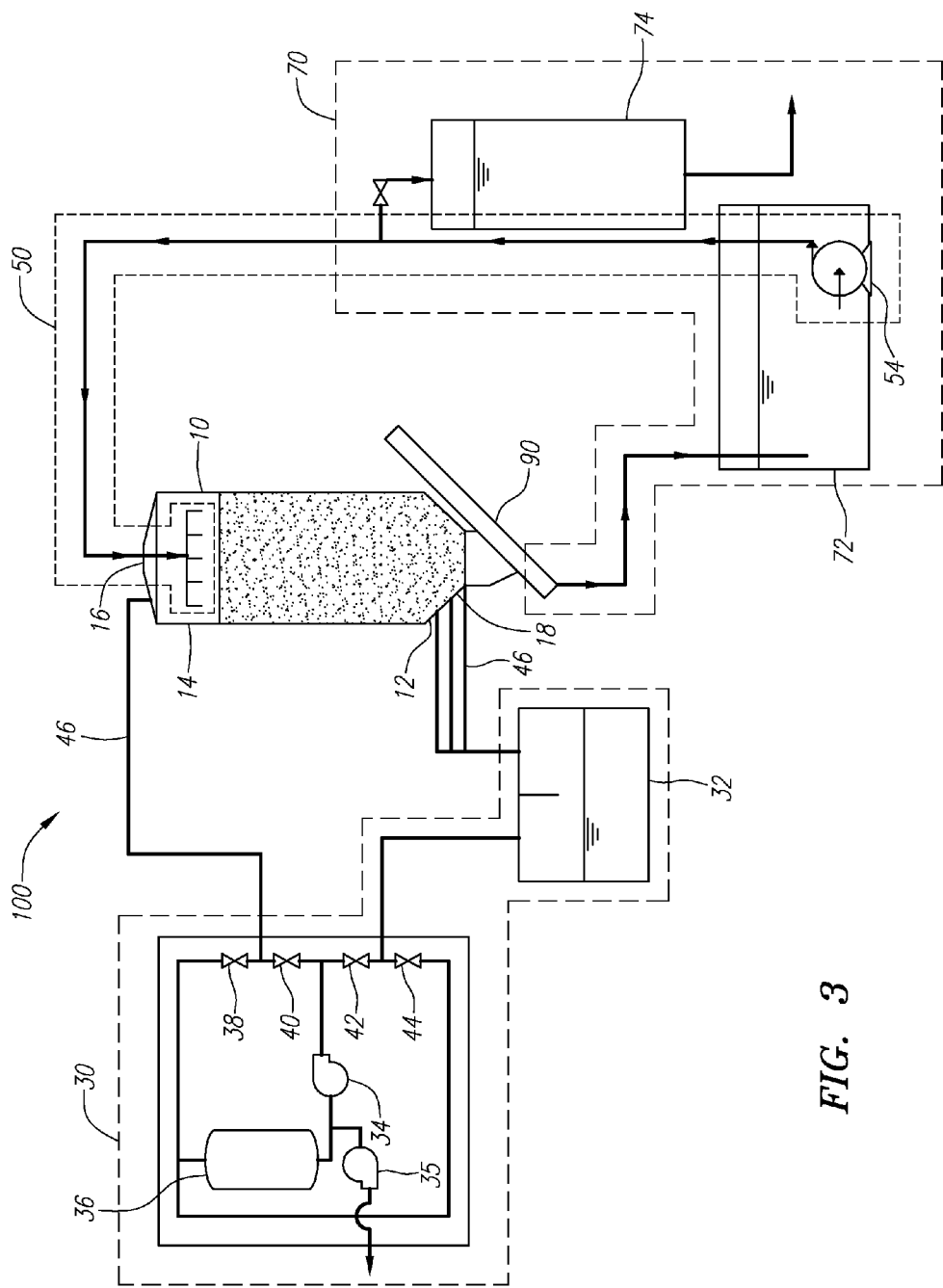
FIG. 3 schematically illustrates a bioreactor for performing static solid state saccharification and/or fermentation of biomass.

FIG. 3 illustrates a schematic view of a bioreactor for performing static solid state fermentation of biomass. As shown in FIG. 3, the gas distribution system further comprises a duct 46, at least one fan 34, and at least one valve 38, 40, 42, and 44. The gas distribution system 30 is in communication with the upper end 14 and the lower end 12 of the vessel 10 via duct 46. Duct 46 may be comprised from a single unit or manufactured from several units. The duct 46 can be made from metal piping, PVC or other plastic piping, conduit, or any other type of tube, canal, pipe, or conduit by which a gas or air can be conducted or conveyed.

The gas distribution system further comprises at least one fan 34 to force the gas through the vessel 10. The at least one fan 34 could likewise be a blower or any other type of device for producing a current of gas or pressure differential, within a duct 46. A single fan or a plurality of fans may be used in the final form. As shown in FIG. 3, a single fan 34 is used for forcing the gas through the vessel 10. In addition to fan 34, an additional fan 35 is shown in the embodiment illustrated in FIG. 3 to allow the bleeding of any excess gas in the gas distribution system 30.

As shown in FIG. 3 four (4) valves 38, 40, 42, and 44 are used but any number of valves may be used in combination to direct the flow of gas through the vessel 10. As shown in FIG. 3 the four (4) valves 38, 40, 42, and 44 allow the gas distribution system 30 to control the flow of gas through the vessel 10 and change the direction of gas flow.

If valves 38 and 42 are closed and valves 40 and 44 are open, the gas leaving the at least one fan 34 is forced through the duct 46 and into the upper end 14 of the vessel 10. The gas continues through the biomass and out the lower end 12 of the vessel 10 returning back to the at least one fan 34. If valves 38 and 42 are open and valves 40 and 44 are closed, the gas is forced to flow in the opposite direction, entering the lower end 12 of the vessel 10 and flowing through the biomass and out the upper end 14 before returning back to the at least one fan 34.

While not required in the composition of a gas distribution system 30, the gas distribution system 30 may further comprise a condensation trap 36, and a liquid trap 32. As shown in FIG. 3, a condensation trap (knock-out pot) 36 may be placed in communication with the duct 46 to control the humidity of the gas and condense out the desired product, such as ethanol, from the gas. The liquid trap (moisture trap) 32, may be used in a similar manner and may also prevent liquid contamination of the gas stream during downward gas flow.

Figure 4:
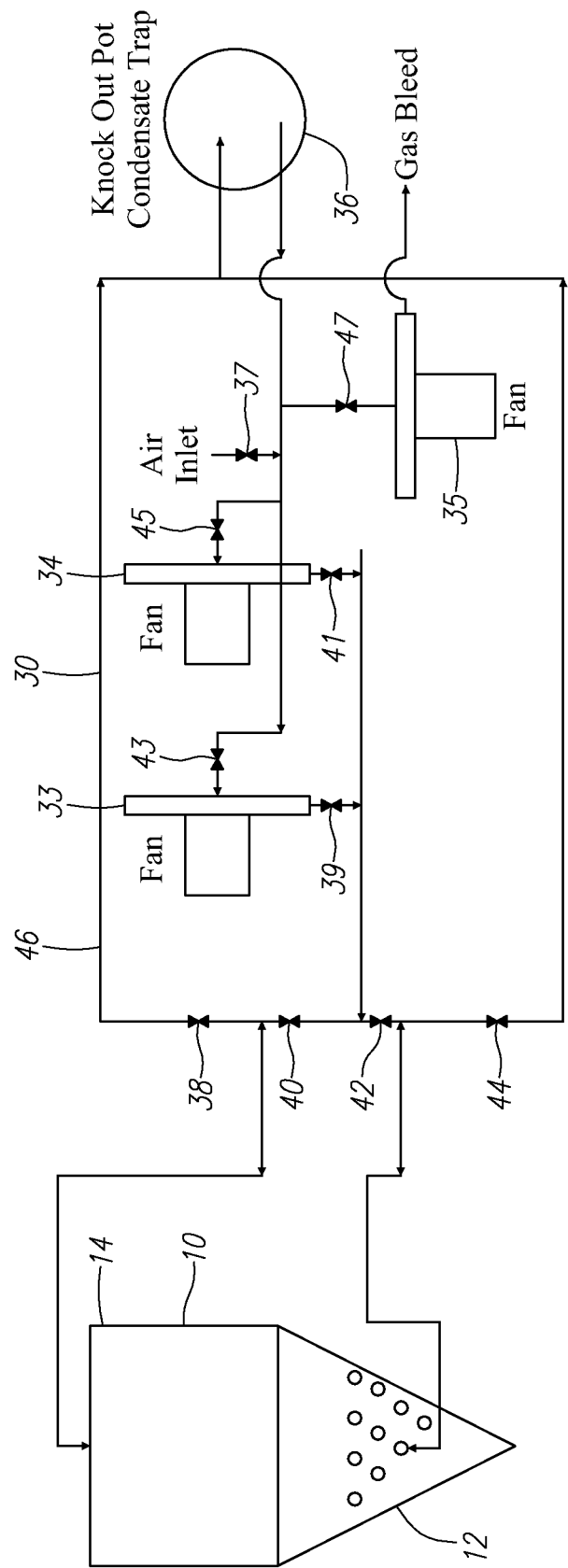
FIG. 4 is a schematic illustrating one embodiment of a gas distribution system for the bioreactor shown in FIG. 3.

FIG. 4 is a schematic illustrating a gas distribution system 30 that can reverse the flow of gas to the vessel 10. As shown in FIG. 4, one embodiment of the gas distribution system 30 that can reverse the flow of gas to the vessel 10 further comprises three (3) fans 33, 34, and 35, and ten (10) valves 37, 38, 39, 40, 41, 42, 43, 44, 45, and 47. Fans 33, and 34 are used in combination to produce the flow of gas through the vessel 10 via duct 46. Valves 39, 41, 43 and 45 are isolation valves added to prevent back pressure from reversing the flow of gas into the fans 33 and 34. Valves 38, 40, 42, and 44 control the direction of flow through the vessel 10 as described above. Gas enters the fans from the condensation trap (knock-out pot) 36 which can be used to remove condensed liquid. Valves 43 and 45 can regulate the flow of gas into the fans 33 and 34 respectively so that either fan can be used or both can be used. Gas leaving the vessel 10 is returned to the condensation trap 36 to complete the recycling loop.

In order to make the fermentation process in the bioreactor 100 more efficient, it is sometimes advantageous to heat the biomass. Adding oxygen can accelerate reactions in the bioreactor and provide additional heat from within. Therefore, in addition to the passive and active heating methods described above, when additional energy is needed, oxygen can be introduced by bleeding air into the gas distribution system 30 through a bleed valve 37. Thus it is possible to heat the biomass and control the temperature during the ethanol production phase. Excess gas can be removed from the system through a vent fan 35. Valve 47 can be used to control the removal of excess gas by the vent fan 35. Valve 37 can be utilized to allow air into the system to enhance oxidation reactions and provide heat. Valve 47 and fan 35 show one embodiment of a system utilized to bleed excess gas from the system. Excess gas can be directed to a newly-loaded bioreactor to purge the initial air atmosphere and replace it with carbon dioxide.

Returning again to FIG. 1, the bioreactor 100 further comprises a liquid distribution system 50 and a liquid collection system 70. The liquid collection system 70 is disposed at the lower end 12 of the vessel 10. Once the biomass is loaded into the vessel 10 the saccharification and/or fermentation processes may begin by introducing water to the bioreactor to initiate effluent discharge. The effluent discharge is collected through a plurality of openings 18 located on the lower end 12 of the vessel 10 by the liquid collection system 70.

The effluent discharge contains ethanol, water, and unfermented sugars. Returning to FIG. 3, the effluent discharge may be collected in a tank 72. As shown in FIG. 3, fluid collection system 70 may further comprise an additional storage tank 74. Additional storage tanks can be used to store excess effluent discharge but are not required.

When sufficient effluent discharge is collected by the liquid collection system 70, it can be added back to the biomass in the vessel 10 by connecting liquid collection system 70 with the liquid distribution system 50. The liquid distribution system 50 may further comprise an irrigation system 52 located at the upper end 14 of the vessel 10. Preferably the irrigation system is a drip irrigation system but can also be a sprayer or other nozzle type that can effectively distribute the effluent discharge over the surface of the biomass located at an upper end 14 of the vessel 10. The liquid distribution system 50 may further comprise a pump 54. The pump 54 is in communication with the effluent discharge in the tank 72. The pump 54 can recycle the effluent discharge from the fluid collection system 70 to the fluid distribution system 50. Recycling effluent discharge allows the sugars that have not been broken down to be re-injected into the vessel 10 for complete fermentation of the remaining sugars. Recycling effluent discharge also allows the recycle of unreacted reagents such as enzymes. Tank 72 also acts as a gas seal and prevents the process gas from leaving via the liquid distribution system. This is accomplished by maintaining a desired hydraulic head in the tank above the discharge of the liquid into the tank that is greater than the gas pressure in vessel 10.

In addition, when the liquid effluent solution is recycled, it may be treated to remove or inactivate deleterious constituents. This can be accomplished by either using a physical filter or by chemical treatment.

In addition to recycling the effluent discharge, the liquid distribution system 50 may be in communication with a plurality of solution tanks containing additives helpful in the saccharification and/or fermentation process. This allows the use of the liquid distribution system to inject important ingredients into the biomass whenever they are needed. These ingredients can be new cultures of microbes, enzymes, nutrients, water, antibiotics, or other essential ingredients to the saccharification and/or fermentation processes.

In addition to the ability to inject important ingredients into the bioreactor 10 and recycle the effluent discharge, the liquid distribution system 50, the liquid collection system 70, and the gas distribution system 30 play important roles in temperature control. Temperature control is a key issue in saccharification and yeast fermentation. The optimum temperature for yeasts used in sugar fermentation such as Saccharomyces cerevisiae is approximately 35° Celsius. At high temperatures the yeast dies and at low temperatures the yeasts' activity is reduced.

During the start of the saccharification and/or fermentation process a method of "bootstrapping" the temperature up can be practiced. At this early stage of the process the temperature may be below the optimum and heat needs to be conserved until the operating temperature is reached.

In order to control the temperature within the vessel 10, the bioreactor 100 of the present invention balances countercurrent liquid and gas flows. Ambient temperature solution is applied to the top of the biomass by the liquid distribution system 50 at the upper end 14 of the vessel 10. The solution is warmed by heat exchange with the warm gas leaving the biomass. The gas undergoes reflux due to cooling at the biomass surface and condenses moisture giving up its heat of condensation to the biomass. As the solution flows downward, it absorbs heat from the biomass and reaches thermal equilibrium. At the lower end 12 of the vessel 10 the incoming cool ambient gas is humidified and the solution leaves the biomass with less energy. The heat capacity of the liquid stream and the gas stream are calculated and the relative flow rates adjusted to maintain the desired temperature and temperature profile.

The relative flow rates of gas and fluid can be expressed as a dimensionless ratio Ga/Gl. This is the ratio of the flow rate of the upward heat carrying gas stream, to the flow rate of the downward heat carrying liquid stream. The flows are expressed as mass per unit cross-sectional area of the reactor per unit time, or commonly as kilograms of fluid per square meter of reactor cross-sectional area per hour (kg/m²/hr). The Ga/Gl ratio is typically and preferably kept between 0.25 and 0.4 depending on what stage the reaction process is in.

Darcy's law is often used to express the flow of liquid through a porous medium. A general form of the equation:

$$Q = -AK\frac{dh}{dl}$$

Q=total discharge (units m³/s)
K=hydraulic conductivity (units m/s)
A=cross-sectional area to the flow (units m²)

$\frac{dh}{dl}$ = is a change in hydraulic head $\Delta h$ over the length $L$, limit of $\Delta h$ as $L$ goes to zero.

Hydraulic conductivity is related to permeability and when a fluid other than water at standard conditions is being used, the conductivity may be replaced by the permeability of the media. The two properties are related by:

$K = k\rho g/\mu = kg/v$ k=permeability, (m²),
μ=fluid absolute viscosity, (N s/m²) and
v=fluid kinematic viscosity, (m²/s).
Substitution of permeability for hydraulic conductivity back into Darcy's law yields:

$$Q = -A\frac{k\rho g}{\mu}\frac{dh}{dl}$$

The hydraulic conductivity of the biomass to gas and liquid can be greatly increased by mixing a bulking agent with the biomass prior to loading into the bioreactor 100. The addition of a bulking agent helps maintain the hydraulic conductivity, counteracting the effects of compaction of the biomass under its own weight and breakdown of the biomass during conversion. The increased hydraulic conductivity eliminates channeling and also prevents the biomass from dramatically reducing in volume as the saccharification and/or fermentation processes occur. This prevents the biomass from pulling away from the walls of the bioreactor, another common cause of channeling.

Hydraulic conductivity is a key factor in the effectiveness of the temperature control of the gas distribution system 30 and the liquid distribution system 50. Adequate hydraulic conductivity is required to ensure that the flows of both gas and liquid can be maintained at the desired levels for the duration of the conversion process.

Bulking agents can be either degradable or non-degradable and can include, for example: sized aggregate, Styrofoam "peanuts" (preferably closed cell), plastic balls, almond shells and hulls, shredded tires, wood chips, and corn cobs. The selection of a bulking agent will depend on numerous factors including availability and also the type of biomass the bulking agent is to be mixed with. When selecting a bulking agent it is important to consider whether it will be inert with respect to the contents of the bioreactor or not. The influences of bulking agents that will somehow participate in the reactions taking place in the bioreactor must be accounted for.

Any bulking agent that when combined with the biomass, can pass the desired liquid and gas flows when under pressure, can be used. It is desired to maintain the ultimate hydraulic conductivity of the biomass to be greater than $10^{-5}$ cm/sec. More preferably the ultimate hydraulic conductivity of the biomass should be maintained greater than $10^{-4}$ cm/sec which will generally limit the gas flow back-pressure to a desired maximum of less than 200 mm of water head. The ultimate hydraulic conductivity is measured at the end of life, after the reactions in the bioreactor have finished. In this manner, it can be verified that the biomass bulking agent mixture maintain the necessary hydraulic conductivity throughout the life of the reaction in the bioreactor.

The quantity of bulking agent added will depend on the bulking agent particle size, size distribution, aspect ratio, shape, type and degradation rate. Table 1 lists some possible bulking agents (BA) to biomass (or feedstock) ratios that were found to have suitable hydraulic conductivity for processing in the bioreactor 100 of the present invention.

Although larger ratios of bulking agent to biomass will tend to have better hydraulic conductivity for any given system, increased use of bulking agent will result in reduced volume of biomass that can be placed in the reactor.

Figure 14:
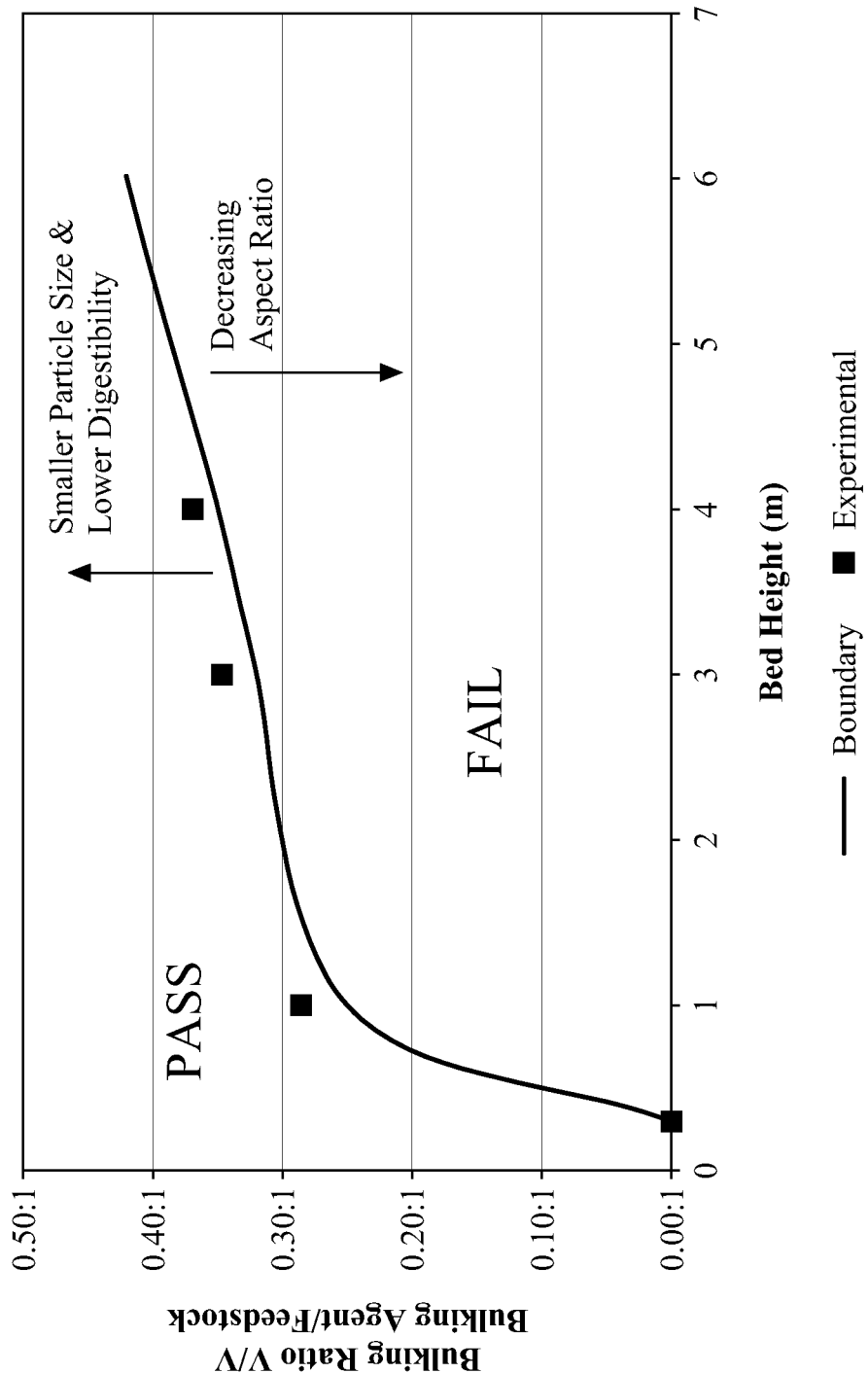
FIG. 14 is a graph showing the effect of bulking agent volume ratio to acceptable bed height in fermentation of waste paper based on irrigation rate.

As noted above, the bulking agent to biomass (or feedstock) volume ratio influences the permeability in solid state fermentation. The graph in FIG. 14 shows the effect of bulking agent volume ratio to acceptable bed height in fermentation of waste paper based on irrigation rate for the experimental data in Table 2 below. As FIG. 14 shows, increasing SSF bed height requires an increased bulking agent to substrate volume ratio because of the increased bed self-weight. In FIG. 14, "Pass" and "Fail" refers to the hydraulic conductivity of the feedstock bed in the SSF reactor. In other words, it is considered to pass if liquid and gas can flow freely through bulked feedstock. The maximum acceptable "pass" irrigation rate for a given bed height is given in Table 2 and generally increases with bed height due to the increased volume and thus increased irrigation rates that are required to maintain the bed within an acceptable process temperature range.

TABLE 2

Effect of Bulking Agent Ratio on Acceptable Bed Height

| Bulking Agent | Substrate | Weight Ratio (BA:BM) | Volume Ratio (BA:BM) | SSSF Ht (m) | Irr. Rate (L/m²/h) |
| --- | --- | --- | --- | --- | --- |
| Plastic Balls | Waste Paper | 0.00:1 | 0.00:1 | 0.3 | 5 |
| Plastic Balls | Waste Paper | 0.44:1 | 0.29:1 | 1 | 5 |
| Plastic Balls | Waste Paper | 0.50:1 | 0.35:1 | 3 | 30 |
| Packing Peanuts | Waste Paper | 0.00:1 | 0.37:1 | 4 | 30 |

TABLE 1

Bulking Agent to Biomass Ratio

| Bulking Agent | Substrate | *Bulking Agent (g) | *Substrate (g) | Ratio (BA:BM) | Column Size | Note |
| --- | --- | --- | --- | --- | --- | --- |
| Plastic Balls | cardboard | 500 | 230 | 2.2 | 1 | 1 m |
| Plastic Balls | cardboard | 250 | 450 | 0.6 | 1 | 1 m |
| Plastic Balls | cardboard | 200 | 450 | 0.4 | 1 | 1 m |
| Plastic Balls | cardboard | 200 | 400 | 0.5 | 1 | 1 m |
| Plastic Balls | cardboard | 250 | 500 | 0.5 | 1 | 1 m |
| Plastic Balls | cardboard | 450 | 900 | 0.5 | 1 | 3 m |
| Tires | cardboard | 700 | 450 | 1.6 | 1 | 1 m |
| Tires | cardboard | 584 | 450 | 1.3 | 1 | 1 m |
| Tires | cardboard | 600 | 450 | 1.3 | 1 | 1 m |
| Tires | cardboard | 400 | 450 | 0.9 | 1 | 1 m |
| Tires | cardboard | 300 | 450 | 0.7 | 1 | 1 m |
| Tires | cardboard | 1500 | 1800 | 0.8 | 1 | 3 m |
| Tires | cardboard | 750 | 1800 | 0.4 | 1 | 3 m |
| Tires | cardboard | 750 | 2000 | 0.4 | 1 | 3 m |
| Plastic Balls | Sludge | 300 | 460 | 0.7 | 1 | 1 m |
| Plastic Balls | Sludge | 300 | 500 | 0.6 | 1 | 1 m |
| Packing Peanuts | Sugar Beet Pulp | 5.46 | 750 | 0.00728 | 1 | BC-1 | or 1:1 by volume |
| Almond Shells | Sugar Beet Pulp | 362 | 362 | 1 | 1 | BC-2 |
| Almond Shells | Fresh Beets | 2000 | 8750 | 0.2 | 1 | BC-3 |
| Almond Shells | Fresh Beets | 2000 | 8750 | 0.2 | 1 | BC-4 |
| Packing Peanuts | Fresh Beets | | | 0.5 | 1** | BC-5 |

*Note:
Bulking Agent and Substrate weights are "as received"
**Based on volume

Typical bulking agent to biomass mass ratios that have proven effective for use in the bioreactor 100 range from 1:5 to 1:1. The corresponding volume ratios will depend on the relative bulk densities of the biomass and bulking agent. Preparing similar tables for other bulking material/feedstock systems will show that the "pass/fail" curve shown in FIG. 14 will shift as illustrated depending on a number of parameters. For example, decreasing feedstock particle size requires a higher bulking agent ratio due to the lower void volume and lower coefficient of permeability of the feedstock. Likewise, feedstocks with high aspect ratios (flat as opposed to round) also require a higher bulking agent ratio. On the other hand, feedstocks that digest completely tend to require a lower bulking agent ratio as the bed voidage increases as the reaction proceeds.

For any given system and reactor bed height, it is desirable to operate as close as possible to the boundary line shown in FIG. 14 in order to maximize the volume of the biomass feedstock that can be included in the bioreactor. Accordingly, the volume of the employed biomass is preferably less than 20%, and more preferably less than 10%, greater than that required by the boundary line for a given material system and bed height.

Although FIG. 14 has been prepared based on irrigation rate, a similar Pass/Fail curve may be prepared based on acceptable "pass" gas flow rates for a given bed height and material system.

The bulking agent can be mixed with the biomass prior to loading into the vessel 10. A variety of mixing devices can be employed including a simple screw mixer, commercial agricultural feed mixer. The goal of the mixing device is to have an evenly distributed mix of bulking agent and biomass.

Figure 5:
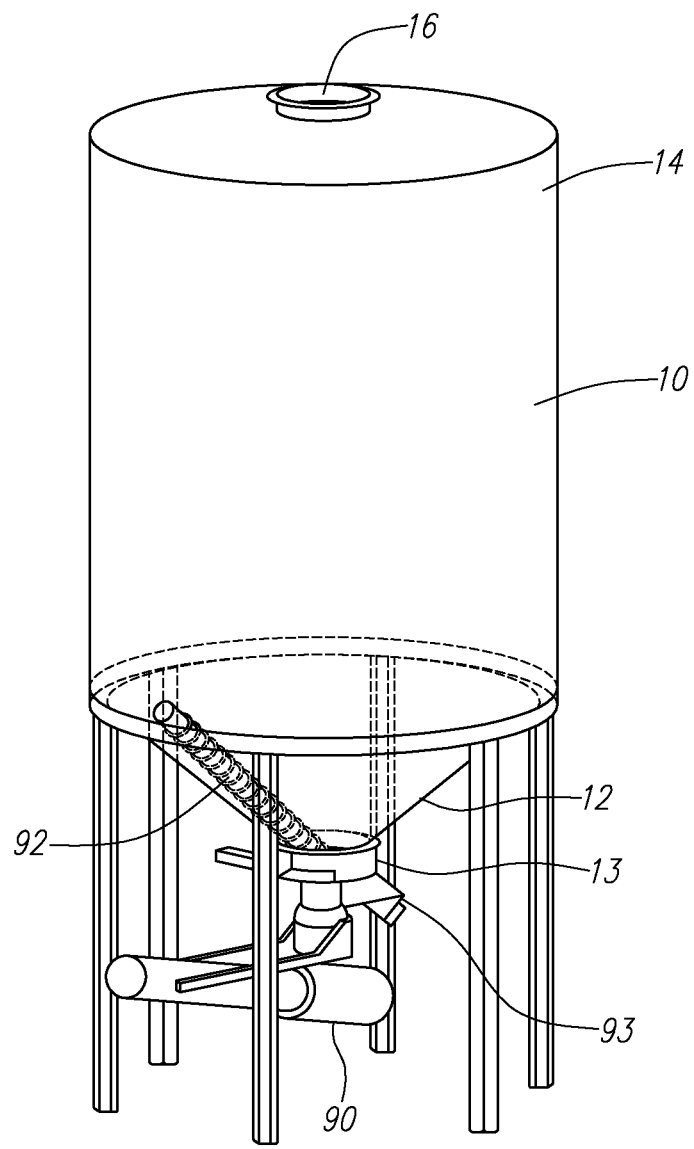
FIG. 5 illustrates a perspective view of a bioreactor vessel with a conical lower end.

FIG. 5 illustrates a perspective view of a vessel for static solid state saccharification and/or fermentation with a conical lower end 12. The conical lower end 12 further comprises a biomass opening or passageway 13 located at the apex of the conical lower end 12. A material removal system 90 further comprises an auger 92 driven by a motor 93 protruding through the biomass opening 13 towards the perimeter of the base of the conically shaped lower end 12. The auger 92 can rotate around the conically shaped lower end 12 to remove biomass from the vessel 10. One advantage of the conically shaped lower end is that it facilitates the natural progression of biomass towards the biomass opening 13 at the apex of the conically shaped lower end 12.

Figure 6:
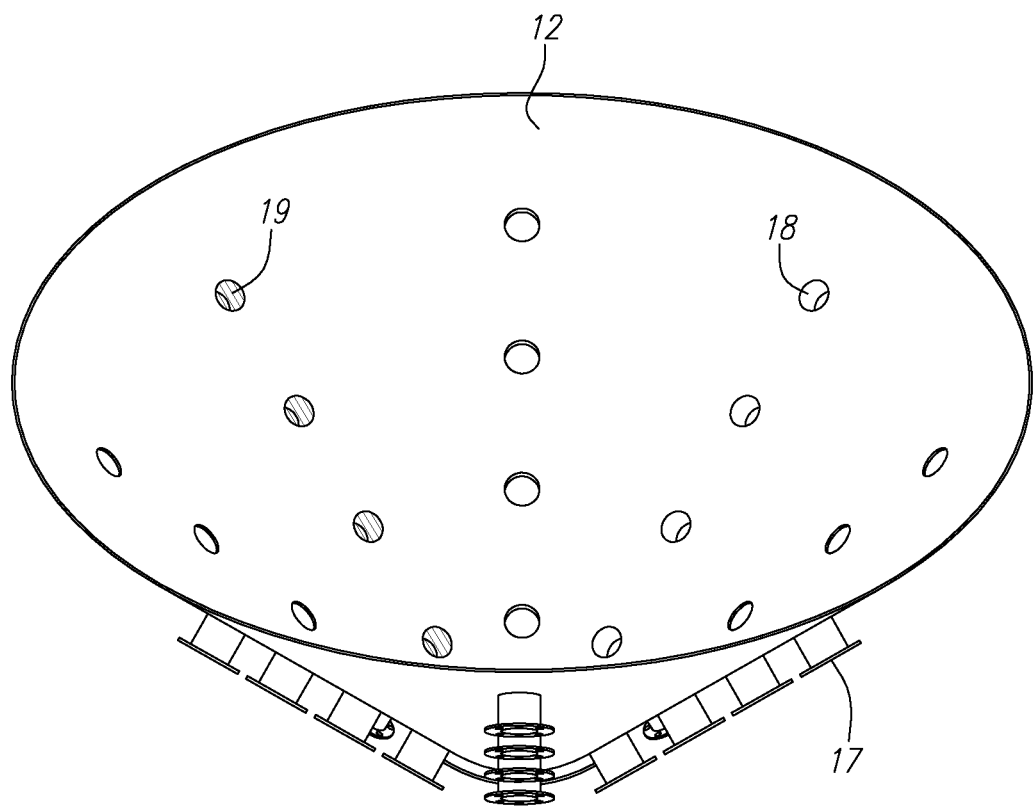
FIG. 6 illustrates a perspective view of a conically shaped lower end with a plurality of openings for gas and liquid distribution/collection.

FIG. 6 illustrates a perspective view of a conically shaped lower end with a plurality of openings. As shown in FIG. 6, the conically shaped lower end 12 can further comprise a plurality of openings 18 located on the lateral surface. The plurality of openings 18 are used to allow the vessel 10 to communicate with the liquid recovery system 70 and the gas distribution system 30. As shown in FIG. 6, the openings are circular; however, the openings can be any shape including, square, rectangular, triangular or other shape. Preferably the openings may be round as it makes attachment of a manifold for communication with the liquid recovery system 70 and gas distribution system 30 easier. As shown in FIG. 6, the plurality of openings 18 consist of eight (8) rows of four (4) openings each; however, any number of openings can be used and in any pattern including random placement. Preferably the plurality of openings are spaced evenly based on the cross-sectional area of biomass above them to allow a more uniform liquid recovery system 70 and gas distribution system 30.

The lower end 12 of the vessel 10 can have numerous openings 18 so that the lower end may be thought of as perforated or resembling a sieve or grate.

As shown, the lower end may further comprise at least one screen 19 used to cover the plurality of openings 18. The at least one screen is used to prevent the biomass in the vessel 10 from passing through any of the plurality of openings 18 and getting into the liquid collection system 70 or the gas distribution system 30.

In FIG. 6, the at least on screen 19 is shown as individual screens covering each opening; however, a single screen may be used to cover all the openings or any combination thereof. For example, the at least one screen can consist of a couple of screens each covering a few openings of the plurality of openings 18.

The wires of the at least one screen 19 can be oriented in any direction in the final form; however, the wires of the at least one screen 19 are preferably oriented so that they run in the direction of material flow during removal. In the case of a conically shaped lower end 12, where material removal occurs at the apex, the wires of the at least one screen 19 would preferably run in a direction from the base perimeter towards the apex. This orientation is preferred in order to prevent the at least one screen 19 from resisting material removal. If the wires of the at least one screen do not run in the direction towards the opening for material removal, they may act like a grate, making material removal difficult. Further, material removal is more likely to cause damage to the wires of the at least one screen 19 if the wires are not oriented in the direction of material removal.

Figure 7:
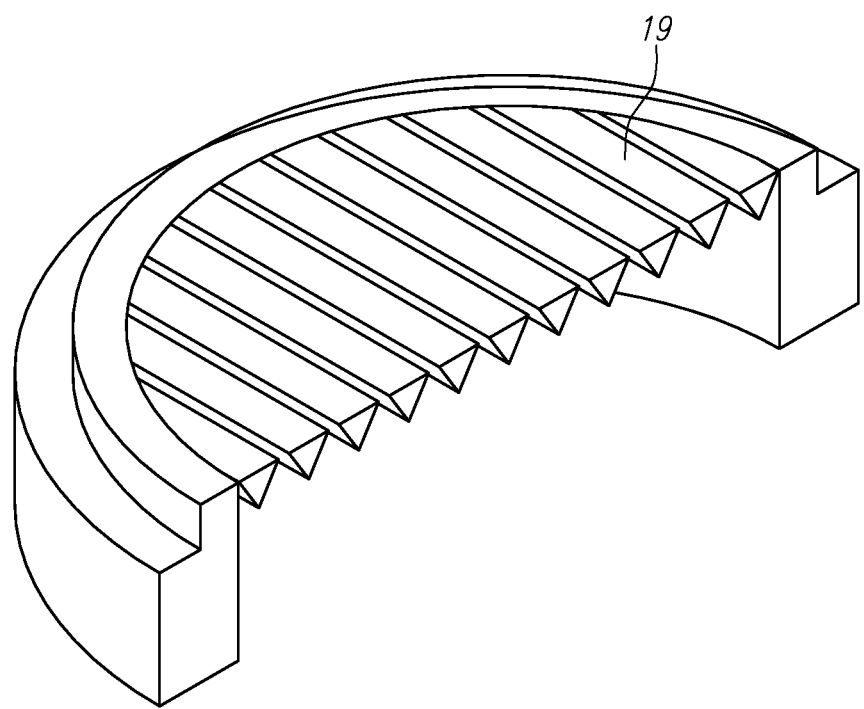
FIG. 7 illustrates a cross section of a screen as used in FIG. 6.

FIG. 7 illustrates a cross section of a screen as used in FIG. 6. As shown in FIG. 7, the screen is a wedge wire screen. This is preferable because any biomass particles that do penetrate the screen will be released by the tapered wedge wire and prevented from obstructing the screen openings and thus be kept from impeding the gas or liquid flow. Although a wedge wire screen is preferable, other types of screens can be used including a wire screen, a mesh screen, a membrane, a filter, or any other device that can prevent the biomass from obstructing any of the plurality of openings 18, and limit the contamination of the liquid recovery system 70 and the gas distribution system 30.

Figure 8:
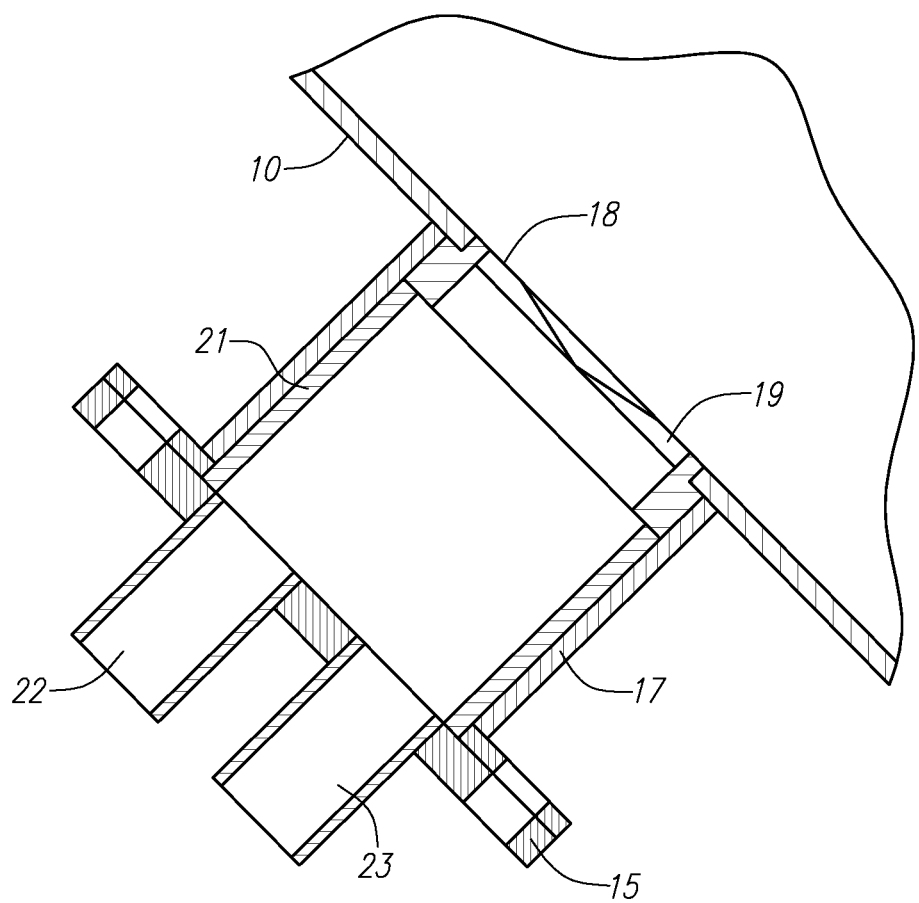
FIG. 8 illustrates a cross section through one of the manifolds shown in FIG. 6 for attaching the liquid recovery system and the gas distribution system to the lower end of the vessel.

FIG. 8 illustrates a cross section of a manifold for attaching the liquid recovery system 70 and the gas distribution system 30 to the lower end of the vessel 10. The gas distribution system 30 and the liquid recovery system 70 are preferably in communication with the lower end 12 of the vessel 10 through the plurality of openings 18. In order to allow easy attachment for communication, a plurality of manifolds 17 may be used. The manifold 17 may be affixed to the lateral wall of the lower end 12 of the vessel 10. The manifold may be welded in place or attached using fasteners but should be sealed to the lower end 12 to prevent any gas or liquid leaks. As shown the manifold 17 contains two ports 22 and 23; however, any number of ports can be used. The ports 22 and 23 are used to connect the gas distribution system 30 and the liquid recovery system 70.

As shown in FIG. 6, the gas distribution system 30 will be in communication with port 22 above port 23 in communication with the liquid recovery system 70. Having the gas distribution system 30 above the liquid recovery system 70 is preferable because the effluent discharge entering the manifold 17 through one of the plurality of openings 18 will naturally gravitate toward the bottom of the manifold 17 and port 23 in communication with the liquid recovery system. This will prevent the effluent discharge from entering the gas distribution system 30.

Also, at least one screen 19, may be used to cover the plurality of openings 18 to prevent the biomass from entering the manifold and thus the liquid recovery system 70 or the gas distribution system 30. The diameter of the ports 22 and 23 is preferably large in proportion to the gap between the wires of the screen to prevent any biomass that passes through the screen 19 from obstructing the flow of gas or liquid. In addition, a gap should be left between the screen 19 and the ports 22 and 23 to allow biomass that is too small to be blocked by the screen, to pass through and not clog the screen and cut off gas and liquid flow.

As shown in FIG. 8, the at least one screen 19 can be held in place by a sleeve 21. The sleeve 21 is inserted inside the manifold 17 and holds the at least one screen 19 up against the plurality of openings 18. The at least one screen 19 is beveled to fit flush with surface of vessel 10. The use of the sleeve 21 prevents the at least one screen 19 from being permanently attached and therefore allows the screen to be removed and cleaned. While a sleeve 21 is shown in FIG. 8 the screen may be held in place in other ways such as welding, clamping, springs, bolts and screws, or other hardware.

The ports are preferably mounted on a flange 15 attached to the manifold 17. This allows the flange 15 to be easily removed for inspection and cleaning of the manifold 17 and the at least one screen 19.

Figure 9:
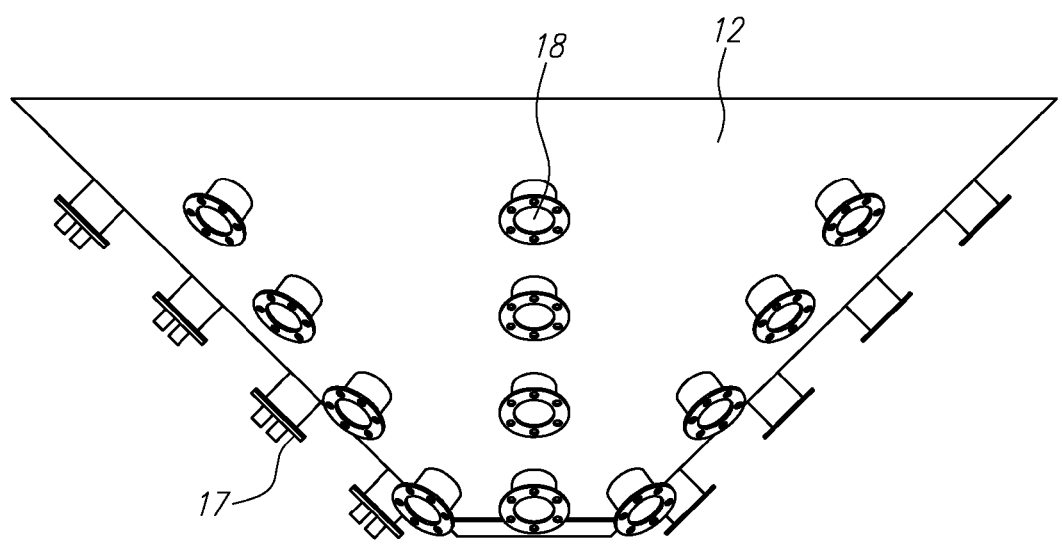
FIG. 9 illustrates a plurality of manifolds attached to a plurality of openings on the lateral surface of the lower end of the vessel.

FIG. 9 illustrates a plurality of manifolds 17 attached to a plurality of openings 18 on the lateral surface of the lower end 12 of the vessel 10.

Figure 10:
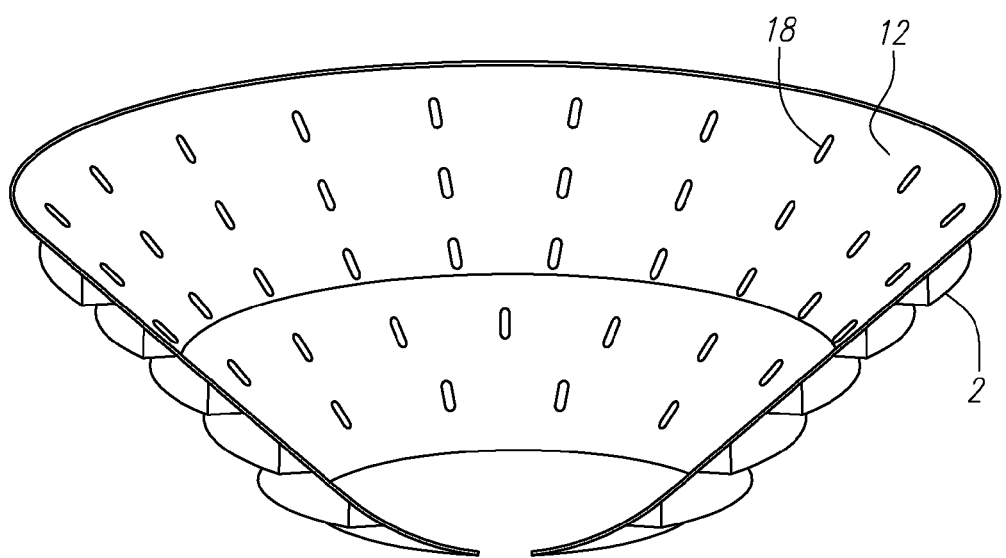
FIG. 10 illustrates a perspective view of an alternative embodiment of a lower end.

While FIG. 6 and FIG. 9 depict a design of the lower end 12 of the vessel 10 that is solid with a plurality of round openings 18, the lower end 12 can have numerous other designs. FIG. 10 illustrates a perspective view of the lower end 12 with a plurality of openings 18 and a plurality of horizontal channels 2. A portion of the lower end 12 has been sectioned away to better show the horizontal channels 2.

Figure 11:
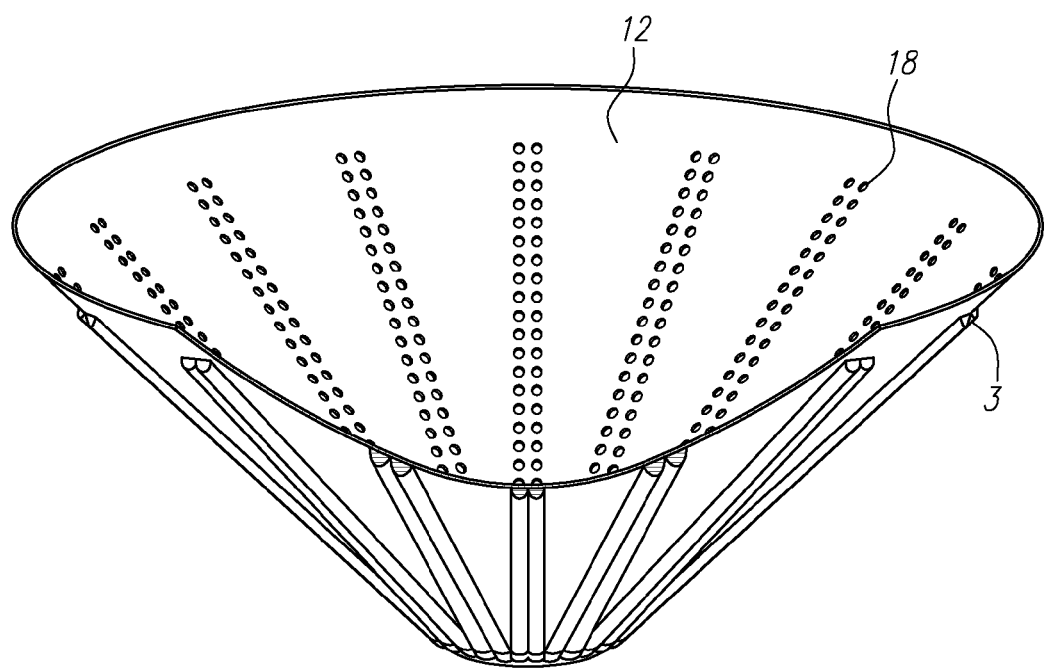
FIG. 11 illustrates a perspective view of another embodiment of a lower end.

FIG. 11 illustrates a perspective view of the lower end 12 with a plurality of openings 18 and a plurality of vertical channels 3. A portion of the lower end 12 has been sectioned away to better show the vertical channels 3.

Figure 12A:
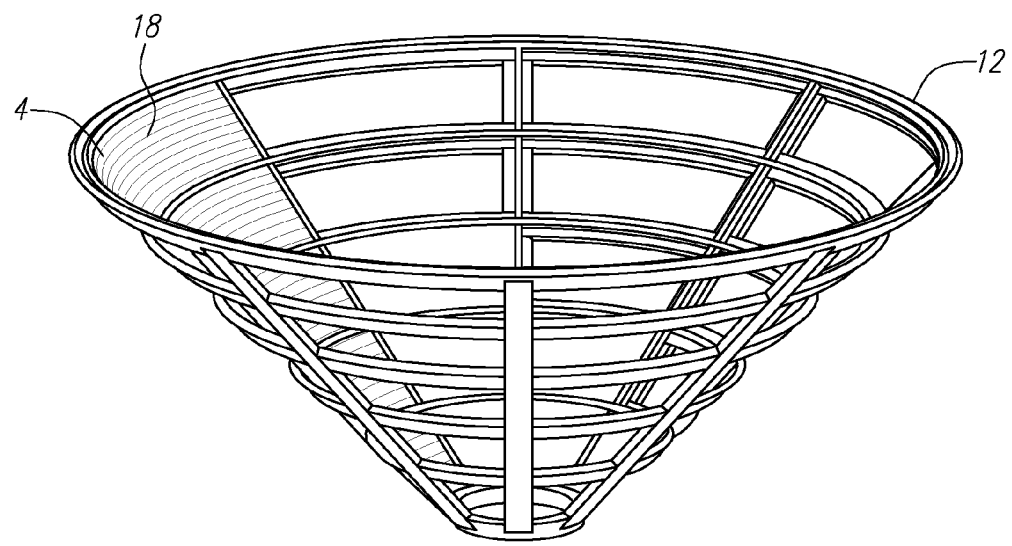
FIG. 12A illustrates yet another embodiment of a conically shaped lower end for the bioreactor of FIG. 5.
Figure 12B:
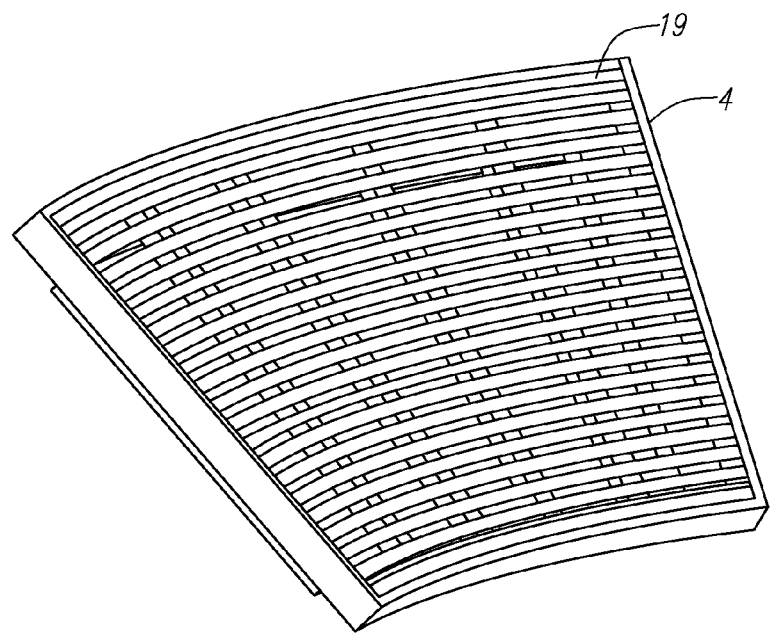
FIG. 12B illustrates a perspective view of a screen panel design for use in the lower end of FIG. 12A.

FIG. 12A illustrates a horizontally oriented panel frame construction for a conically shaped lower end of a bioreactor. While the lower end 12 may be made from a solid piece, it may also be made using a panel frame design. The frame of the lower end 12 holds a plurality of horizontal panels 4. The plurality of horizontal panels 4 creates a plurality of openings 18 in the lower end 12 of the vessel 10. FIG. 12B illustrates a panel design for use in a horizontal panel frame designed lower end 12 for a bioreactor 100. As shown in FIG. 12B, the plurality of panels 4 have at least one screen 19 to prevent the biomass from entering into the plurality of horizontal panels 4. The horizontal panels 4 are connected to gas distribution 30 and liquid recovery systems 70.

Figure 13A:
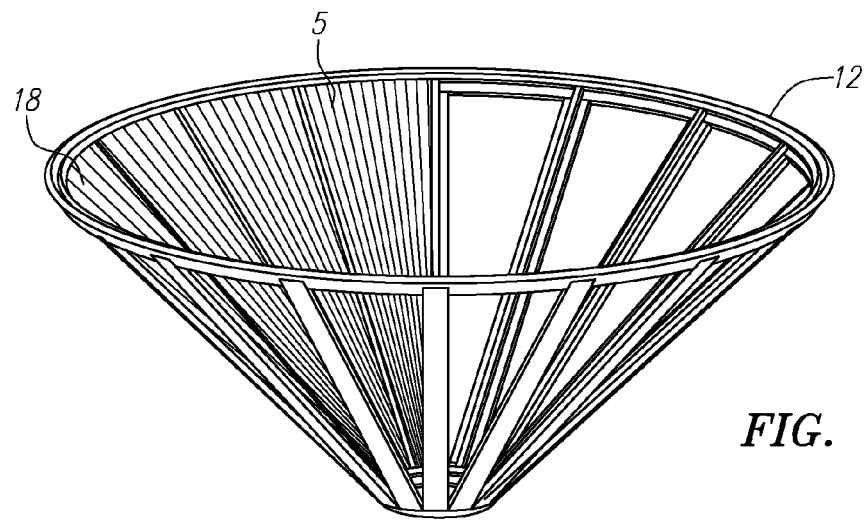
FIG. 13A illustrates still a further embodiment of a conically shaped lower end for the bioreactor of FIG. 5.
Figure 13B:
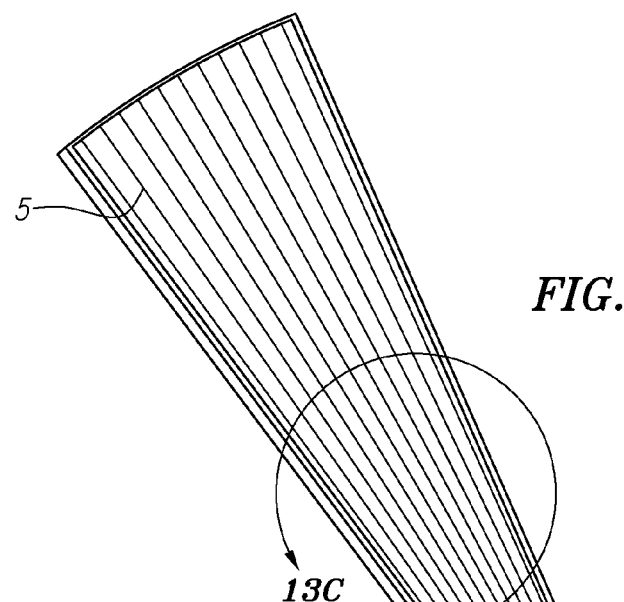
FIG. 13B illustrates a perspective view of a screen panel design for use in a vertically oriented panel frame designed lower end for a bioreactor.
Figure 13C:
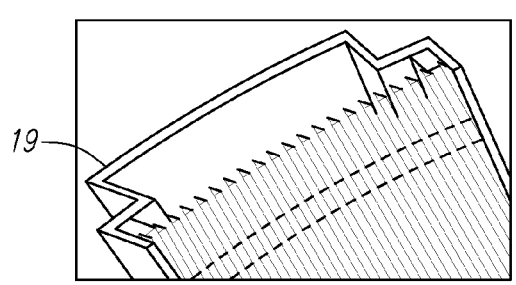
FIG. 13C illustrates an enlarged cross-sectional view shown in perspective of the portion of the screen circled in FIG. 13B.

FIG. 13A illustrates a vertically oriented panel frame construction for a conically shaped lower end of a bioreactor. The frame of the lower end 12 holds a plurality of vertical panels 5. The plurality of vertical panels 5 creates a plurality of openings 18 in the lower end 12 of the vessel 10. FIG. 13B illustrates a panel design for use in a vertical panel frame designed lower end for a bioreactor. As shown in FIG. 13B, the plurality of vertical panels 5 have at least one screen 19 to prevent the biomass from entering into the plurality of vertical panels 5. The at least one screen 19 is preferably oriented with the wires running vertically because it allows for the material to be more easily removed from the vessel 10. If the wires are running in the horizontal direction as in FIG. 12B the at least one screen 19 resists material removal and acts more like a grate when the biomass is removed. FIG. 13C illustrates a perspective view of the at least one screen 19 of FIG. 13B.

What is claimed is:

1. A static solid state bioreactor, the bioreactor comprising:
a vessel having an upper end and a conically shaped lower end, the upper end having a sealable opening;
a gas distribution system in communication with the upper end and the lower end of the vessel;
a liquid distribution system in communication with the vessel at the upper end;
a liquid recovery system in communication with the vessel at the lower end; and
a material removal system disposed at the lower end of the vessel extending through a biomass residue removal opening for removing biomass residue from the vessel, the biomass residue removal opening located at an apex of the conically shaped lower end,
wherein the vessel further comprises a plurality of openings located on the lower end, and
wherein the gas distribution system communicates with the vessel at the lower end through the plurality of openings.

2. The bioreactor of claim 1, wherein the liquid recovery system communicates with the vessel at the lower end through the plurality of openings.

3. The bioreactor of claim 1, wherein the material removal system further comprises an auger driven by a motor wherein the auger protrudes into the vessel through the biomass residue removal opening at the apex and extends up towards a perimeter of a base of the conically shaped lower end.

4. The bioreactor of claim 1, wherein the plurality of openings located at the lower end are formed in the lateral surface of the conically shaped lower end.

5. The bioreactor of claim 4, wherein the liquid recovery system is in communication with the lower end of the vessel through the plurality of openings.

6. The bioreactor of claim 4, further comprising at least one screen disposed on the lower end of the vessel and covering the plurality of openings.

7. The bioreactor of claim 4, further comprising a plurality of screens, each screen being configured to fit within and cover one of the plurality of openings in the lower end of the vessel.

8. The bioreactor of claim 1, wherein the gas distribution system further comprises:
at least one fan;
a first duct in communication with the upper end of the vessel and the fan; and
a second duct in communication with the lower end of the vessel and the fan.

9. The bioreactor of claim 8, wherein the gas distribution system further comprises at least one valve, wherein the at least one valve is arranged in the gas distribution system to permit the selective connection of an intake and an output from the at least one fan to the first duct and the second duct and thereby change a direction of a gas flow through the vessel.

10. The bioreactor of claim 1, wherein the liquid recovery system is in communication with the liquid distribution system and further wherein a liquid effluent from the bioreactor can be recycled.

11. The bioreactor of claim 6, wherein the at least one screen is a wedge wire screen.

12. The bioreactor of claim 11, wherein the wedge wire screen further comprises a plurality of wires oriented to run towards a direction of material removal.

13. The bioreactor of claim 10, wherein the liquid effluent is treated by physical means before recycling.

14. The bioreactor of claim 10, wherein the liquid effluent is treated by chemical means before recycling.

15. The bioreactor of claim 10, further comprising a means for treating the effluent discharge to improve quality before recycling.

16. A static solid state bioreactor, the bioreactor comprising:

a vessel having an upper end, a conically-shaped lower end, and a plurality of openings formed in the lateral surface of the conically shaped lower end, the upper end having a sealable opening;

a gas distribution system in communication with the upper end and the lower end of the vessel;

a liquid distribution system in communication with the vessel at the upper end;

a liquid recovery system in communication with the vessel at the lower end;

a material removal system disposed at the lower end of the vessel for removing biomass residue from the vessel; and a plurality of screens, each screen being configured to fit within and cover one of the plurality of openings in the lower end of the vessel, wherein the gas distribution system communicates with the vessel at the lower end through the plurality of openings.

17. The bioreactor of claim 16, wherein the liquid recovery system communicates with the vessel at the lower end through the plurality of openings.

18. The bioreactor of claim 16, wherein the material removal system extends through a biomass residue removal opening located at an apex of the conically shaped lower end.

19. The bioreactor of claim 18, wherein the material removal system further comprises an auger driven by a motor wherein the auger protrudes into the vessel through the biomass residue removal opening at the apex and extends up towards a perimeter of a base of the conically shaped lower end.

20. The bioreactor of claim 16, wherein the gas distribution system further comprises:
   at least one fan;
   a first duct in communication with the upper end of the vessel and the fan; and
   a second duct in communication with the lower end of the vessel and the fan.

21. The bioreactor of claim 20, wherein the gas distribution system further comprises at least one valve, wherein the at least one valve is arranged in the gas distribution system to permit the selective connection of an intake and an output from the at least one fan to the first duct and the second duct and thereby change a direction of a gas flow through the vessel.

22. The bioreactor of claim 16, wherein the liquid recovery system is in communication with the liquid distribution system and further wherein a liquid effluent from the bioreactor can be recycled.

23. The bioreactor of claim 16, wherein the plurality of screens comprise a wedge wire screen.

24. The bioreactor of claim 23, wherein the wedge wire screen further comprises a plurality of wires oriented to run towards a direction of material removal.

* * * * *